(12) United States Patent
Eacho et al.

(10) Patent No.: US 7,217,727 B2
(45) Date of Patent: May 15, 2007

(54) PHOSPHOLIPASE INHIBITORS

(75) Inventors: Patrick Irving Eacho, Indianapolis, IN (US); Patricia Sue Foxworthy-Mason, Indianapolis, IN (US); Ho-Shen Lin, Indianapolis, IN (US); Jose Eduardo Lopez, Fishers, IN (US); Marian Kazimierz Mosior, Carmel, IN (US); Michael Enrico Richett, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 162 days.

(21) Appl. No.: 10/544,908

(22) PCT Filed: Mar. 25, 2004

(86) PCT No.: PCT/US2004/006095

§ 371 (c)(1),
(2), (4) Date: Aug. 10, 2005

(87) PCT Pub. No.: WO2004/094393

PCT Pub. Date: Nov. 4, 2004

(65) Prior Publication Data

US 2006/0116409 A1    Jun. 1, 2006

Related U.S. Application Data

(60) Provisional application No. 60/459,833, filed on Apr. 1, 2003.

(51) Int. Cl.
*A61K 31/423*    (2006.01)
*C07D 261/20*    (2006.01)
(52) U.S. Cl. ...................... 514/379; 548/241
(58) Field of Classification Search ................ 548/241; 514/379
See application file for complete search history.

(56) References Cited

FOREIGN PATENT DOCUMENTS

| DE | 2257750 A | 5/1974 |
|----|-----------|--------|
| EP | 0684242 A1 | 11/1995 |
| EP | 0897903 A3 | 2/1999 |

*Primary Examiner*—Joseph K. McKane
*Assistant Examiner*—Michael P. Barker
(74) *Attorney, Agent, or Firm*—James B. Myers; Francis O. Ginah

(57) ABSTRACT

A novel class of 3-oxo-3H-benzo[d]isoxazole carboxamide compounds is disclosed together with the use of such compounds for inhibiting hepatic lipase and/or endothelial lipase activity for treatment, amelioration or prevention of hepatic lipase and/or endothelial lipase mediated diseases.

11 Claims, No Drawings

PHOSPHOLIPASE INHIBITORS

REFERENCE TO RELATED APPLICATIONS

This application is submitted as a United States national phase entry, pursuant to 35 U.S.C. §371, of PCT/US2004/006095, filed on Mar. 25, 2004, which claims the benefit of U.S. provisional patent application Ser. No. 60/459,833, filed Apr. 1, 2003 each of which is incorporated by reference herein.

FIELD OF THE INVENTION

This invention relates to novel 3-oxo-3H-benzo[d]isoxazole carboxamide compounds useful for the treatment and/or prevention of diseases mediated by phospholipases including hepatic and endothelial lipase.

BACKGROUND OF THE INVENTION

Hepatic lipase plays an important role in lipid metabolism. Hepatic lipase is a glycoprotein that functions as a ligand or as an enzyme of approximately 65 Kda, which has been shown to catalyze the hydrolysis of lipids including triglycerides, diglycerides and phospholipids in native lipoproteins. It has also been shown to. facilitate the selective uptake of cholesterol from high-density lipoproteins and the removal of remnant particles by the liver (Jonathan C. Cohen, et al *Biochemistry* 1992, 31: 8544–8551 and Neve et al *Biochemistry J.* 1998, 330:701–706).

Other studies showing the inverse relationship of HDL and hepatic lipase activity include for example, Haffner S. M. et al., "Studies on the metabolic mechanism of reduced high density lipoproteins during anabolic steroid therapy," *Metabolism* 1983; 32:413–420; Applebaum-Bowden D, et al., "The Dyslipoproteinemia of Anabolic steroid therapy: increase in hepatic triglyceride lipase precedes the decrease in high density lipoprotein—2 cholesterol," *Metabolism* 1987; 36:949–952; and Kantor M. A. et al., "Androgens reduce HDL-2 cholesterol and increase hepatic triglyceride lipase activity," *Med. Sci. Sport exercise* 1985; 17:462–465.

The inverse relationship between hepatic lipase activity and the level of HDL-cholesterol, particularly type-2 HDL-cholesterol, can be used to advantage in up-regulating the Level of HDL cholesterol-the good cholesterol.

Endothelial lipase (EL) is a newly described member of the lipase gene family. Like hepatic lipase, endothelial lipase has been implicated in the hydrolysis of HDL phospholipids and in the reduction of HDL-cholesterol in vivo. In experiments using hepatic lipase knockout mice the infusion of a polyclonal antibody inhibitory to endothelial lipase resulted in a marked increase in HDL-cholesterol levels (Rader, D. J., et al *Journal of Clinical Investigation* (2003), 111(3) 357–362.

Chan, et al, *Proceedings of the National Academy of Sciences* U.S.A. (2003), 100(5), 2748–2753, has also reported the inverse relation between endothelial lipase and HDL-cholesterol.

Given the preceding information, it is desirable to discover and develop compounds that increase HDL levels by methods that may include inhibiting the activity of hepatic lipase and/or endothelial lipase in order to treat, prevent and/or ameliorate the effects of hepatic lipase and/or endothelial lipase mediated diseases. Few therapeutically desirable agents are available to accomplish the task of increasing HDL levels hence the need for and utility of the present invention.

SUMMARY OF THE INVENTION

The present invention provides a 3-oxo-3H-benzo[d]isoxazole carboxamide compound of formula (I):

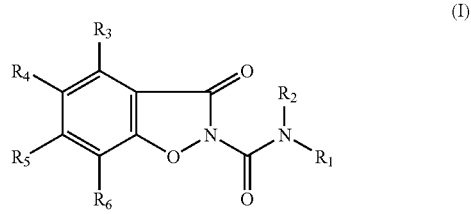

(I)

wherein;

$R_1$ is selected from the group consisting of hydrogen, $C_1$–$C_{13}$alkyl, $C_1$–$C_{20}$haloalkyl, $C_2$–$C_{13}$alkenyl, $C_2$–$C_{20}$alkynyl, $C_1$–$C_{13}$alkoxyalkyl, $C_1$–$C_{13}$alkylamine, $C_1$–$C_5$alkylcycloalkyl, $C_1$–$C_5$alkylcycloalkenyl, cycloalkyl, cycloalkenyl, $C_1$–$C_5$alkylaryl, $C(O)C_1$–$C_6$alkyl, and alkylheterocyclic radical; wherein each of the alkyl, alkenyl, alkynyl, cycloalkyl, cycloalkenyl, and heterocyclic groups may be further substituted with 1, 2, or 3 substituents independently selected from $C_1$–$C_6$alkyl, halo, haloalkyl, COOH, $C(O)OC_1$–$C_6$alkyl, $C(O)C_1$–$C_6$alkyl, hydroxy, and amino groups;

$R_2$ is hydrogen;

$R_3$, $R_4$, $R_5$, and $R_6$, are each independently selected from hydrogen, halo, hydroxy, amino, $C_2$–$C_{12}$alkyl, $C_1$–$C_{12}$haloalkyl, $C_2$–$C_{12}$alkenyl, $C_2$–$C_{12}$alkynyl, $C_2$–$C_{12}$alkylaryl, $C_1$–$C_{12}$alkylcycloalkyl, $C_1$–$C_{12}$alkylcycloalkenyl, COOH, $C(O)C_1$–$C_6$alkyl, $C(O)OC_1$–$C_6$alkyl, $C(O)NR^aR^b$, $C_1$–$C_{12}$alkylheterocyclic, phenyl, or aryl; wherein $R^a$ and $R^b$ are independently selected from $C_1$–$C_5$alkyl, $C_2$–$C_5$alkenyl, phenyl, benzyl, and $C_1$–$C_5$alkylcycloalkyl; or a pharmaceutically acceptable salt, solvate prodrug or enantiomer thereof.

The present invention provides the use of a 3-oxo-3H-benzo[d]isoxazole carboxamide compound of formula (I):

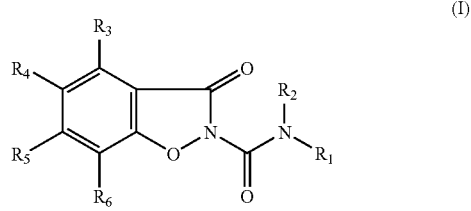

(I)

wherein $R_1$ is selected from the group consisting of hydrogen, $C_1$–$C_{13}$alkyl, $C_1$–$C_{20}$haloalkyl, $C_2$–$C_{13}$alkenyl, $C_2$–$C_{20}$alkynyl, $C_1$–$C_{13}$alkoxyalkyl, $C_1$–$C_{13}$alkylamine, $C_1$–$C_5$alkylcycloalkyl, $C_1$–$C_5$alkylcycloalkenyl, cycloalkyl, cycloalkenyl, $C_1$–$C_5$alkylaryl, $C(O)C_1$–$C_6$alkyl, and alkylheterocyclic radical; wherein each of the alkyl, alkenyl, alkynyl, cycloalkyl, cycloalkenyl, and heterocyclic groups may be further substituted with 1, 2, or 3 substituents independently selected from $C_1$–$C_6$alkyl, halo, haloalkyl, COOH, $C(O)OC_1$–$C_6$alkyl, $C(O)C_1$–$C_6$alkyl, hydroxy, and amino groups;

$R_2$ is hydrogen;

$R_3$, $R_4$, $R_5$, and $R_6$, are each independently selected from hydrogen, halo, hydroxy, amino, $C_2$–$C_{12}$alkyl, $C_1$–$C_{12}$haloalkyl, $C_2$–$C_{12}$alkenyl, $C_2$–$C_{12}$alkynyl, $C_2$–$C_{12}$alkylaryl, $C_1$–$C_{12}$alkylcycloalkyl, $C_1$–$C_2$alkylcycloalkenyl, COOH, C(O)$C_1$–$C_6$allyl, C(O) O$C_1$–$C_6$alkyl, C(O)NR$^a$R$^b$, $C_1$–$C_{12}$alkylheterocyclic, phenyl, or aryl; wherein R$^a$ and R$^b$ are independently selected from $C_1$–$C_5$alkyl, $C_2$–$C_5$alkenyl, phenyl, benzyl, and $C_1$–$C_5$alkylcycloalkyl; or a pharmaceutically acceptable salt, solvate prodrug or enantiomer thereof for the treatment, prevention and/or amelioration of diseases mediated by hepatic lipase and/or endothelial lipase activity.

The present invention provides the use of 3-oxo-3H-benzo[d]isoxazole-N-carboxamide compounds of formula I as inhibitors of mammalian hepatic lipase and/or endothelial lipase.

The present invention also relates to the use of compounds of formula I useful in the treatment and/or prevention of hepatic lipase and/or endothelial lipase mediated diseases, comprising administration of a therapeutically effective amount of a compound of formula (I), or a pharmaceutically acceptable salt or solvate to a patient in need thereof.

The present invention also relates to the use of a novel 3-oxo-3H-benzo[d]isoxazole carboxamide compound of formula I to increase or mediate the increase of high-density lipoproteins (HDL) upon administration to a patient in need thereof.

The present invention provides a pharmaceutical composition containing any of the compounds of the invention.

The present invention also relates to the use of a pharmaceutical formulation comprising a compound of formula I and a carrier and/or diluent for the treatment and/or prevention of hypercholesterolemia.

The present invention relates to the use of a compound of formula I for the manufacture of a medicament for the treatment and/or prevention of hepatic lipase and/or endothelial lipase-mediated diseases comprising administering a therapeutically effective amount of a compound of formula (I), or a pharmaceutically acceptable salt, solvate to a patient in need thereof.

DEFINITIONS

The terms, "mammal" and "mammalian" include human and domesticated quadrupeds.

The phrase, "hepatic lipase and/or endothelial lipase mediated-diseases" refers to diseases symptomatic of low HDL levels, caused by, modulated by, exacerbated by or induced directly or indirectly by elevated hepatic lipase and/or endothelial lipase activity, and include for example, hypercholesterolemia, hyperlipidemia, stroke, hypertriglyceridemia, atherosclerosis and related diseases. Treatment and/or prevention of such diseases comprises administering to a mammal in need of such treatment a therapeutically effective amount of the compound of formula I in an amount sufficient to inhibit, ameliorate and/or prevent hepatic lipase and/or endothelial lipase activity and to thereby inhibit or prevent the deleterious effects of hepatic lipase and/or endothelial lipase activity.

The term "Active Ingredient" as used herein refers to a compound(s) of Formula (I) or a pharmaceutically acceptable salt, solvate, prodrug, racemate or enantiomer thereof either as the pure compound or delivered as a pharmaceutical formulation or a pharmaceutical composition. The pharmaceutical composition or formulation containing a compound of the invention and other compound(s) or treatment regimens useful for the treatment and/or prevention of diseases associated with or exacerbated by hepatic lipase and/or endothelial lipase activity (combination drugs) are contemplated to be within the meaning of the term "Active Ingredient(s)."

The term, "3-oxo-3H-benzo[d]isoxazole", or "3-oxo-3H-benzo[d]isoxazole nucleus" as used herein refers to a nucleus (having numbered positions) with the structural formula (X):

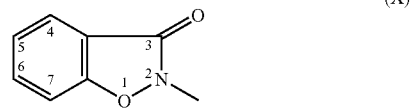

The 3-oxo-3H-benzo[d]isoxazole compounds of the invention employ certain defining terms as follows:

The term, "alkyl" by itself or as part of another substituent means, unless otherwise defined, a straight or branched chain monovalent hydrocarbon radical, such as for example, methyl, ethyl, n-propyl, isopropyl, n-butyl, tertiary butyl, sec-butyl, n-pentyl, and n-hexyl.

The term, "alkenyl" employed-alone or in combination with other terms means a straight chain or branched monovalent hydrocarbon group having the stated number ranges of carbon atoms, and typified by groups such as vinyl, propenyl, crotonyl, isopentenyl, and various butenyl isomers.

The term, "hydrocarbyl" means an organic group containing only carbon and hydrogen.

The term "carboxy" means an organic group containing only carbon and-oxygen, i.e. the group —C(O)—.

The term, "halo" means fluoro, chloro, bromo, or iodo.

The term, "heterocyclic radical" or "heterocyclic group" refers to radicals or groups derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, benzo(b) thiophenyl, carbazolyl, norharmanyl, azabenzo(b)thiophenyl, benzofuranyl, dibenzofuranyl, dibenzothiophenyl, indazolyl, imidazo(1,2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiophenyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The terms "($C_1$–$C_{12}$)alkylcyclopentyl," "($C_1$–$C_{12}$)alkyl-cyclohexyl," or "($C_5$–$C_{20}$)alkylheterocyclic" represent respectively a ($C_1$–$C_{12}$)alkyl, ($C_1$–$C_{12}$)alkyl, or ($C_1$–$C_{12}$) alkyl group attached to a cylopentyl, cyclohexyl, and heterocyclic group wherein the entire group is attached to the 3-oxo-3H-benzo[c]isoxazole nucleus (X) at the alkyl terminus. The pattern as above is reflective of the naming system or connotation employed herein. For example, the term $C_1$–$C_{12}$ alkylcycloalkyl means the $C_1$–$C_{12}$ alkyl group is substituted on the cycloalkyl group and the composite group is attached to the nucleus at the alkyl terminus. For the purpose of the present invention, the term "cycloalkyl" or "(C₃–C₈)cycloalkyl" without more implies a cycloalkyl group having from 3 to 8 carbon atoms.

The term "substituted group" is an organic group substituted with one or more "non-interfering" substituents. By "non-interfering" is meant that the group is suitable chemically and stability-wise to occupy the designated position and perform the designated or intended role. Thus unsuitable groups are excluded from the definition of "non-interfering".

As used herein the terms "group", "radical" or "fragment" are synonymous and are intended to indicate functional groups or fragments of molecules attachable to a bond or other fragments of molecules. For example acetamide group represent the acetamide fragment or radical. Structures of groups, radicals or fragments unattached to the 3-oxo-3H-benzo[d]isoxazole nucleus have been drawn to show the first line as a connecting bond only. Thus, the group

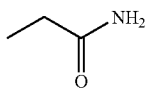

represents the acetamide radical or group, not the propanamide radical unless otherwise indicated.

The term, "alkylene chain of 1 or 2 carbon atoms" refers to the divalent radicals, —CH₂—CH₂— and —CH₂—.

THE 3-oxo-3H-benzo[d]isoxazole Compounds of the Invention

The present invention provides the use of a novel class of 3-oxo-3H-benzo[d]isoxazole compounds useful as inhibitors of hepatic lipase and/or endothelial lipase activity for the treatment, amelioration and/or prevention of hepatic lipase and/or endothelial lipase-mediated diseases.

The compounds of the invention are represented by the general formula (I) and include pharmaceutically acceptable salts, or enantiomers, prodrugs or solvates thereof.

Preferred Subgroups of Compounds of Formula (1):

Preferred R₁ Substituents:

The preferred group for R₁ is a substituted or unsubstituted group selected from the group consisting of C₂–C₁₃alkyl, C₂–C₁₃alkenyl, C₂–C₁₀alkoxyalkyl, C₅–C₁₄cycloalkenyl, cycohexylmethyl, cyclopentylmethyl, cyclohexylethyl, phenyl, naphthyl, toluyl, xylenyl, indenyl, stilbenyl, terphenylyl, diphenylethylenyl, phenyl and cyclohexenyl.

More preferred, as the group R₁ is a benzyl group substituted with one, two or three groups independently selected from methyl, ethyl, isopropyl, tert-butyl, isobutyl, methylcyclopentyl, cylopentyl, cyclohexyl, methycyclohexyl, cyclohexylmethyl, cycloheptylmethyl, phenyl and benzyl. Most preferred R₁ group is a benzyl group substituted with one, two or three groups independently selected from methyl, ethyl, isopropyl, isobutyl, tert-butyl.

Preferred R₃, R₄, R₅, and R₆ Substituents:

R₃, R₄, R₅, and R₆ are preferably selected independently from the group consisting of hydrogen, halo, hydroxy, amino, C₁–C₄alkyl, C₂–C₄alkenyl, —CO—(C₁–C₄)alkyl, —COOH, —COO—(C₁–C₄)alkyl, —O—(C₁–C₄)alkyl, —S—(C₁–C₃)alkyl, —C₅–C₂₀cycloalkyl, —CF₃, halo, —NO₂, and —CN.

A preferred compound of the invention is a compound selected from the group consisting of:
3-oxo-3H-benzo[d]isoxazole-2-carboxylic acid ethylamide,
3-oxo-3H-benzo[d]isoxazole-2-carboxylic acid butylamide,
3-oxo-3H-benzo[d]isoxazole-2-carboxylic acid hexylamide,
3-oxo-3H-benzo[d]isoxazole-2-carboxylic acid (5-methylhexyl)amide,
3-oxo-3H-benzo[d]isoxazole-2-carboxylic acid (5-methylhexyl)amide,
3-oxo-3H-benzo[d]isoxazole-2-carboxylic acid octylamide,
3-oxo-3H-benzo[d]isoxazole-2-carboxylic acid cyclohexylmethyl-amide,
3-oxo-3H-benzo[d]isoxazole-2-carboxylic acid 4-nitro-phenyl ester,
3-oxo-3H-benzo[d]isoxazole-2-carboxylic acid cyclohexylmethyl-amide,
3-oxo-3H-benzo[d]isoxazole-2-carboxylic acid benzylamide,
3-oxo-3H-benzo[d]isoxazole-2-carboxylic acid 2-methylbenzylamide,
3-oxo-3H-benzo[d]isoxazole-2-carboxylic acid 3-methylbenzylamide,
3-oxo-3H-benzo[d]isoxazole-2-carboxylic acid 4-methylbenzylamide,
3-oxo-3H-benzo[d]isoxazole-2-carboxylic acid 2-trifluoromethyl-benzylamide,
3-oxo-3H-benzo[d]isoxazole-2-carboxylic acid 2-fluorobenzylamide,
3-oxo-3H-benzo[d]isoxazole-2-carboxylic acid 4-fluorobenzylamide,
3-oxo-3H-benzo[d]isoxazole-2-carboxylic acid 2-ethyl-benzylamide,
3-oxo-3H-benzo[d]isoxazole-2-carboxylic acid 3-ethyl-benzylamide,
3-oxo-3H-benzo[d]isoxazole-2-carboxylic acid 4-tert-butyl-benzylamide,
3-oxo-3H-benzo[d]isoxazole-2-carboxylic acid 2-isopropyl-6-methyl-benzylamide,
3-oxo-3H-benzo[d]isoxazole-2-carboxylic acid 3-methoxybenzylamide,
3-oxo-3H-benzo[d]isoxazole-2-carboxylic acid 4-methoxybenzylamide,
3-oxo-3H-benzo[d]isoxazole-2-carboxylic acid 2-ethoxybenzylamide,
3-oxo-3H-benzo[d]isoxazole-2-carboxylic acid 3-ethoxybenzylamide,
3-oxo-3H-benzo[d]isoxazole-2-carboxylic acid 4-ethoxybenzylamide,
3-oxo-3H-benzo[d]isoxazole-2-carboxylic acid phenethylamide, and a pharmaceutically acceptable salt, solvate, racemate, enantiomer or diastereomeric mixture thereof.

More preferred compounds of the invention are represented by the formulae (C1), (C2), (C3), (C4), and (C5):

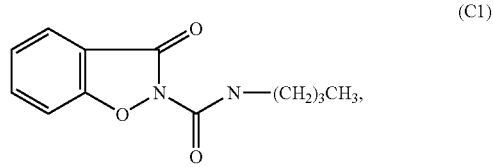

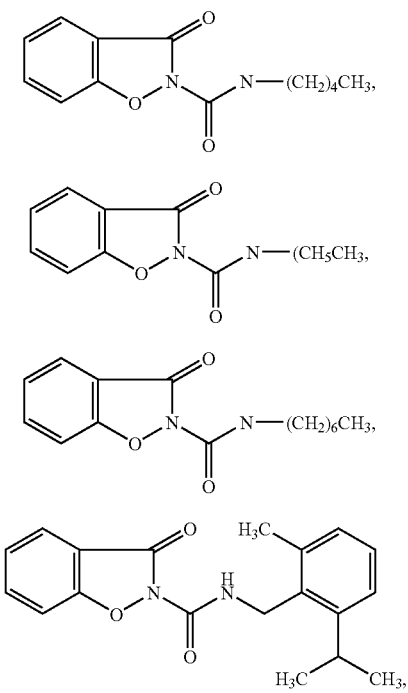

or a pharmaceutically acceptable salt, solvate, racemate, enantiomer, prodrug or diastereomeric mixture thereof.

The salts of the 3-oxo-3H-benzo[d]isoxazole carboxamide compounds represented by formula (I), are an additional aspect of the invention.

In those instances when the compound of the invention possesses acidic or basic functional groups, various salts may be formed which are more water soluble and more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.* 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of stereoisomers and diastereomers, because they have different melting points, different boiling points, and different solubilities and can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs* pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA;. Item No. 25,099-6).

Morpholinylethyl ester prodrugs may be prepared by reaction of the sodium salt of a compound of formula (I) (in a medium such as dimethylformamide) with 4-(2-chloroethyl)morpholine hydrochloride (available from Aldrich Chemical Co., Milwaukee, Wis. USA, Item No.C4, 220-3).

METHODS FOR PREPARING COMPOUNDS OF THE INVENTION

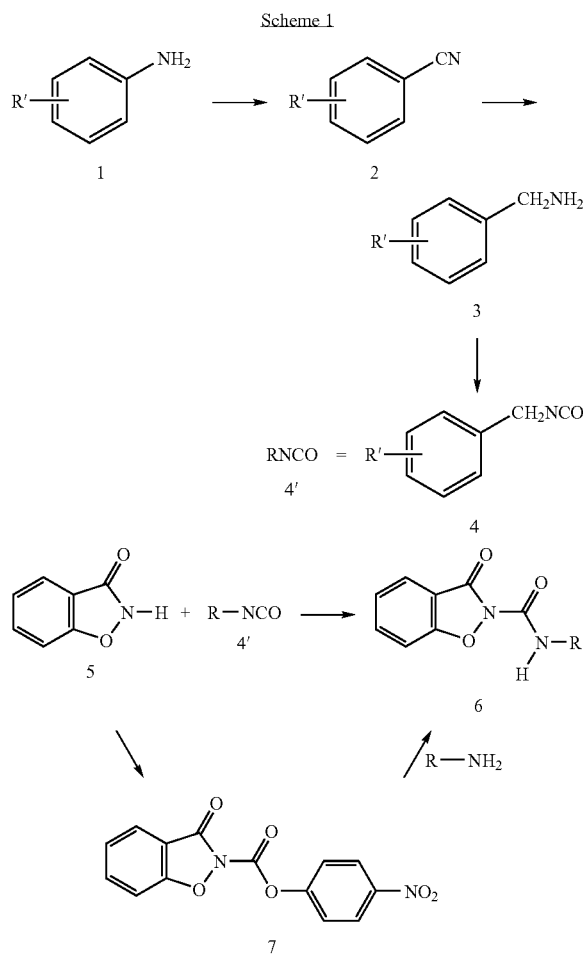

Scheme 1 depicts a protocol for preparing 3-oxo-3H-benzo[d]isoxazole compounds of the invention starting from an aniline derivative 1 (Aldrich Chemical Co. Milwaukee U.S.A, and other fine chemical suppliers) or substituted analogs thereof. The starting material 1 may be diazotized by reaction with tert-butylnitrite (available from Aldrich Chemical Company, Milwaukee, USA) to afford a diazotized intermediate which reacts with incipient cyanide ion from added copper cyanide to afford the nitrile compound 2. The nitrile 2 is reduced to afford the substituted methylamine compound 3. The substituted methylamine compound 3 is converted to the isocyanate compound 4 in an aprotic solvent such as anhydrous dichloromethane. The conversion of the methylamino compound 3 to the isocyanate compound 4 is accomplished using triphosgene in the presence of a proton scavenger such as triethylamine. The isocyanate 4 or 4' is reacted with a solution of benz[d]isothiazol-3-one in a suitable solvent e.g., anhydrous dichloromethane at temperatures ranging from about 10 to 60° C. The isocyanate 4or 4' is then reacted with 3-oxo-3H-benzo[d]isoxazole 5 or substituted analogs thereof to afford the compound(s) of the invention such as compound 6. 3-oxo-3H-benzo[d] isoxazole 5 also called 1,2-benzoisothiazolin-3-one is available from commercial suppliers, such as MDA Chemicals Limited, Willow Mill, Caton, Lancaster LA2 9RA, UK. Analogs of 3-oxo-3H-benzo[d]isoxazole may be obtained by methods described in the examples and/or known to one of skill in the art.

Compounds of formula I wherein all of $R_3$, $R_4$, $R_5$, and $R_6$ are not hydrogen are made starting with purchased starting materials having the requisite substituents or by methods known to one of skill in the art or described in the experimental section.

METHODS OF USING THE COMPOUNDS OF THE INVENTION

The 3-oxo-3H-benzo[d]isoxazole carboxamide compounds described herein are believed to achieve their beneficial therapeutic action principally by direct inhibition of hepatic lipase and/or endothelial lipase activity.

The method of the invention for inhibiting hepatic lipase and/or endothelial lipase activity with a therapeutically effective amount of a 3-oxo-3H-benzo[d]isoxazole carboxamide compound of Formula (I) including a combination thereof, a salt or a prodrug derivative thereof is as described herein.

Another aspect of this invention relates to inhibition or prevention of "Hepatic Lipase Mediated Diseases" such as hypercholesterolemia, hyperlipidemia, stroke, congenital heart failure, hypertension, hypertriglyceridemia, hyper alphaliproteinemia, atherosclerosis and related diseases as described earlier. The method comprises of administering to a mammal (including a human) in need of such treatment a therapeutically effective amount of a 3-oxo-3H-benzo[d] isoxazole carboxamide compound of the invention.

As previously noted the compounds of the invention are useful for inhibiting hepatic lipase and/or endothelial lipase activity. By the term, "inhibiting" is meant to be the prevention or therapeutically significant reduction in release of hepatic lipase and/or endothelial lipase by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or ameliorative or prophylactic effect will, of course, be determined by the particular circumstances surrounding the clinical presentation, including, for example, the-compound administered, the route of administration and the condition being treated. Typical daily doses will contain a non-toxic dosage level of from about 0.01 mg/kg to about 50 mg/kg of body weight of an active compound of this invention.

Preferably, compounds of the invention per Formula (I) or pharmaceutical formulations containing these compounds are in unit dosage form for administration to a mammal. The unit dosage form can be a capsule or tablet itself, or the appropriate number of any of these. The quantity of Active Ingredient in a unit dose of composition may be varied or adjusted from about 0.1 to about 500 milligrams or more according to the particular treatment involved. It should be appreciated that it may be necessary to make routine variations to the dosage depending on the age and condition of the patient. The dosage will also depend on the route of administration.

A compound of the invention may be administered by a variety of routes including oral, aerosol, transdermal, subcutaneous, intravenous, intramuscular, or intranasal as appropriate for the particular patient.

Pharmaceutical formulations of the invention are prepared by combining (e.g., mixing) a therapeutically effective amount of the 3-oxo-3H-benzo[d]isoxazole carboxamide compound of the invention together with a pharmaceutically acceptable carrier or diluent therefor. The present pharmaceutical formulations are prepared by known procedures using well-known and readily available ingredients.

In making the compositions of the present invention, the Active Ingredient will usually be admixed with a carrier, or diluted by a carrier, or enclosed within a carrier, which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art may be used. In such a formulation, the carrier may be a solid, liquid, or mixture of a solid and a liquid. For example, for intravenous injection the compounds of the invention may be dissolved at a concentration of 2 mg/ml in a 4% dextrose/0.5% Na citrate aqueous solution. Solid form formulations include powders, tablets and capsules. A solid carrier can be one or more substance, which may also act as flavoring agents, lubricants, solubilizers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. A preferred tablet formulation for oral administration is one that affords rapid dissolution in the mouth of a patient in need thereof.

In powders the carrier is a finely divided solid, which is in admixture with the finely divided Active Ingredient. In tablets the Active Ingredient is mixed with a carrier having the necessary binding properties in suitable proportions and compacted in the shape size and color desired. The powders and tablets preferably contain from about 1 to about 99 weight percent of the Active Ingredient(s), which is the novel compound(s) of this invention. Suitable solid carriers are magnesium carbonate, magnesium stearate, talc, sugar lactose, pectin, dextrin, starch, gelatin, tragacanth, methylcellulose, sodium carboxymethyl cellulose, low melting waxes, and cocoa butter.

Sterile liquid form formulations include suspensions, emulsions, syrups and elixirs.

The Active Ingredient can be dissolved or suspended in a pharmaceutically acceptable carrier, such as sterile water, sterile organic solvent or a mixture of both. The Active Ingredient may be dissolved in a suitable organic solvent, for instance aqueous propylene glycol. Other compositions can be made by dispersing the finely divided Active Ingredient in aqueous starch or sodium carboxymethyl cellulose solution or in a suitable oil.

The following pharmaceutical formulations 1 through 8 are illustrative only and are not intended to limit the scope of the invention in any way. "Active Ingredient", refers to a compound or compounds of Formula (I) or a pharmaceutically acceptable salt, solvate, racemate or enantiomer thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active Ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing .60 mg of Active Ingredient, are made as follows:

Active Ingredient 60 mg

| Starch | 45 mg |
| --- | --- |
| Microcrystalline cellulose | 35 mg |
| Polyvinylpyrrolidone (as 10% solution in water) | 4 mg |
| Sodium carboxymethyl starch | 4.5 mg |

| -continued | |
|---|---|
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active Ingredient, are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active Ingredient, are made as follows:

| Active Ingredient | 225 mg |
|---|---|
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active Ingredient per 5 ml dose, are made as follows:

| Active Ingredient | 50 mg |
|---|---|
| Sodium carboxymethyl cellulose | 50 mg |
| Syrup | 1.25 ml |
| Benzoic acid solution | 0.10 ml |
| Flavor | q.v. |

| -continued | |
|---|---|
| Color | q.v. |
| Purified water to total | 5 ml |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active Ingredient | 100 mg |
|---|---|
| Isotonic saline | 1,000 ml |

The solution of the above ingredients generally is administered intravenously to a subject at a rate of 1 ml per minute.

The abbreviations, symbols and terms used in the examples have the following meanings.

Ac=acetyl
Anal.=elemental analysis
calcd=calculated
Cpd.=compound
DMF=dimethylformamide
DMSO=dimethylsulfoxide
Et=ethyl
EtOAc=ethyl acetate
EtOH=ethanol
EtSH=ethanethiol
ESIMS=Electrospray Ionization Mass Spectrometry
FAB=Fast Atom Bombardment (Mass Spectroscopy)
FDMS=field desorption mass spectrum
Hex=hexanes
HL=Hepatic Lipase
HPLC=High Performance Liquid Chromatograph
HRMS=high resolution mass spectrum
IR=Infrared Spectrum
Me=methyl
MeI=methyl iodide
MeOH=methanol
MPLC=Medium Pressure Liquid Chromatography
NMR=Nuclear Magnetic Resonance
PPA=polyphosphoric acid
Rochelle's Salt=potassium sodium tartrate
RPHPLC=Reversed Phase High Performance Liquid Chromatography
SiO$_2$ silica gel
SM=starting material
Temp.=temperature
TFA=trifluoroacetic acid
THF=tetrahydrofuran
TLC=thin layer chromatography Hepatic Lipase Phospholipase Assay Compounds of the present invention were found to be efficacious in-vitro in inhibiting the release of hepatic lipase and/or endothelial lipase. Efficacy was determined by testing various compounds of the invention in a hepatic lipase and/or endothelial lipase assay discussed below, and disclosed in U.S. patent application Ser. No. 09/609, 871 filed Jul. 3, 2000 incorporated herein in its entirety for U.S Patent office purposes.

Reagents
Substrate Buffer A: 100 mM Hepes, pH 8.3 at 37° C.
Substrate Buffer B: 100 mM Hepes, pH 8.3 at 37° C. with 6.83 mM Triton X100
ThioPEG: Molecular wt. of 540
Recombinant Hepatic Lipase
Thiophospholipid: about 0.42 mM thiophospholipid in chloroform
DTNB Solution: about 50 nM DTNB in DMSO (dimethyl sulfoxide)

Hepes Buffer A

For Hepes Buffer A,.there is 2.4 g Hepes/100 mL water. Therefore 36 grams of Hepes is dissolved in 1500 mL of water. The mix solution's pH is adjusted to pH83 at 37° C. and brought up to 1500 mL with water. 500 mL of Buffer A is retained for the Protein Buffer.

Hepes Buffer B

To the remaining 1000 mL of Hepes Buffer A, 4.49 g of Triton X-100 is added and then the combination mixed on a stir plate. It is optimal that stock Buffer A not be too cold or Triton X-100 will take a long time to go into solution ThioPEG Substrate Solution For 0.42 mM substrate stock, use 0.227 mg of thioPEG/mL of Substrate Buffer B. Approximately 20 mg of sn-1 thiol substituted Phosphatidyl Ethylene Glycol (see Examples for preparation method) is weighed into a vial, such as a scintillation vial. Enough chloroform should be added to make a 2.043 mg/mL solution. Sonicate the solution briefly until well dissolved. Next, pipette 1 mL of chloroform/substrate solution into each scintillation vial. This should give enough substrate for one full 96 well plate. Each vial is dried with nitrogen until solvent removed, swirling each vial simultaneously such that a thin film of substrate will be easily reconstituted in each buffer. Each vial is then frozen.

Daily stock preparation is performed for 9 mL of substrate (one microtiter plate). On the day of the assay, the substrate vial is removed from the freezer and combined with 9 mL of pre-warmed (37° C.) substrate buffer (the final concentration is 0.227 mg/mL). Place the buffer in a 37° C. water bath. Sonicate for 5 minutes or vortex until solution is clear before use.

Enzyme Solution

The enzyme is stored at −80° C. in 100 or 50 μL portions. A 0.406 mg/mL recombinant hepatic lipase and/or endothelial lipase stock requires a 50-fold dilution. Therefore, to a 50 μl or 100 μl enzyme aliquot, 2450 μl or 4900 μl, respectively, of substrate Buffer A (protein buffer) should be added. The enzyme should then be stored on ice until ready to use. The protein concentration of enzyme is about 0.406 mg/mL.

DTNB Solution

To make a 20 mg/mL stock solution, 2–3 mg of DTNB is weighed and then mixed with an appropriate amount of 100% DMSO (dimethyl sulfoxide) to make the desired concentration. This mixture is sonicated for five minutes.

The above solution should be diluted 10 fold with substrate Buffer B (concentration now 2 mg/mL). Then to the thioPEG substrate solution, add 60 μl of dilute DTNB per mL of thioPEG substrate solution. Thus for 9 mL of substrate, 540 microliters of dilute DTNB (final concentration in substrate solution=0.11 mg/mL).

Table 1 below shows final assay volumes and concentrations of various components used following the above procedure.

TABLE 1

Final Assay Volumes and Concentrations

| Component | Assay Volume | Final Concentration |
|---|---|---|
| HL | 10 μl | 12.5 nM |
| Test Cpd. | 10 μl | Varies |
| ThioPEG Substrate (stock = 0.42 mM + substrate buffer) | 80 μl | 90 mM Hepes 5.8 mM TX100 0.336 mM ThioPEG (0.06 mol fraction) 0.088 mM DTNB/mL |

Hepatic Lipase Phospholipase Assay

Sample Preparation

The test compound is dissolved in pure DMSO at 1 μM (1000 nM). As shown below in Table 2, assay concentrations are 10, 1, 0.1, 0.33, 0.011, 0.0037, 0.0012 and 0.00041 μM. Table 2 shows the assay concentrations and the corresponding volume of stock and 10% DMSO for each concentration.

TABLE 2

Assay concentrations for compound preparation

| Concentration (μM) | Assay Conc. (μM) | Microliters of stock solution | Diluents |
|---|---|---|---|
| 100 | 10 | 50 of 1 mM in straight DMSO | 450 μl of WATER |
| 10 | 1 | 5 μl of 100 μM | 450 μl 10% DMSO |
| 1 | 0.1 | 50 μl of 10 μM | 450 μl 10% DMSO |
| 0.33 | 0.033 | 200 μl of 1 μM | 400 μl 10% DMSO |
| 0.11 | 0.011 | 200 μl of 0.33 μM | 400 μl 10% DMSO |
| 0.037 | 0.0037 | 200 μl of 0.11 μM | 400 μl of 10% DMSO |
| 0.012 | 0.0012 | 200 μl of 0.037 μM | 400 μl of 10% DMSO |
| 0.0041 | 0.00041 | 200 μl of 0.012 μM | 400 μl of 10% DMSO |

Assay Procedure

Using a spectrometer, DTNB is used as a thiol coloring reagent with an incubator temperature of 37° C. Substrate Buffer B is placed in a 37° C. water bath to pre-warm. The substrate is removed from the freezer and 9 mL of substrate Buffer B, 100 mM Hepes, 6.83 mM Tx-100) is added, sonicated for 5 min. and then kept in a 37° C. water bath. Dilutions of the test compound are next made in preparation for assay.

10 μl of the diluted test compound are transferred via pipette into the wells. Control wells receive 10 μl each of 10% DMSO and enzyme solution, while blank wells receive 10 microliters of 10% DMSO and 10 microliters of saline (no enzyme).

Next, DTNB is weighed and diluted to 20 mg/mL with DMSO. The DTNB is then diluted 10 fold with the substrate Buffer B. 540 μl of diluted DTNB is added to 9 ml of ThioPEG and mixed well.

The stock enzyme is diluted with Buffer A. Next, 10 microliters of protein solution is added to each well except the blank, and the wells mixed. The stock solution and test compounds are incubated at 37° C. for 10 min. At 10 minutes, 80 microliters of substrate are added to each well.

The plate is then placed in the spectrometer and read at 412 nM every 2 minutes for 30 minutes.

Results of hepatic lipase inhibition assay

| Compounds | IC50 (nM) |
|---|---|
| (benzo[d]isoxazol-3-one with N-C(O)-NH-(CH2)4CH3) | 62.8 +− 2.6 |
| (benzo[d]isoxazol-3-one with N-C(O)-NH-(CH2)5CH3) | 81.0 +− 2.2 |
| (benzo[d]isoxazol-3-one with N-C(O)-NH-(CH2)6CH3) | 109.8 +− 9.3 |
| (benzo[d]isoxazol-3-one with N-C(O)-NH-benzyl) | 60.0 |

Hepatic lipase (HL) and endothelial lipase (EL) were expressed from AV12 cells. Aliquots from one day's collection of media were stored at −70° C. Activity was measured for both enzymes in conditioned media, (non-purified) where they were tested on the same plate with Thio PEG substrate (0.06 mol fraction, 7.24 mM total lipid), at 37° C. and 30 minutes. The HL, at 1×, had an OD of 14.7. The OD for EL at 1× was 6.029. Therefore, when HL was used in studies where it was compared to EL, the HL was at 0.25× and EL was used at 1×. All experiments were done in triplicate with enzyme from conditioned media.

Kinetic experiments for EL were done varying the total lipid with a constant 0.044 mol fraction determining that a 10 mM total lipid was optimal. In addition, kinetic experiments varying the mol fractions with a constant total lipid showed that 0.03 mol fraction was optimal. Each experiment was run three times.

Experiments to determine proper pH of the substrate to be used with EL were performed at 37° C. with the above-mentioned conditions. The enzyme was tested at pH 7.0, 7.4 and 8.3. The order of addition of reagents/enzyme was as follows: 10 µL of 10% DMSO, 80 µL of substrate and 10 µL of enzyme. Data represents an average of three experiments.

Temperature of the assay was varied from 26.9° C. to 37° C. with the above-mentioned conditions. This was the temperature of the incubation during the 30-minute read. The pH of the substrate was 8.3. The order of addition of reagents/enzyme was as follows: 10 µL of 10% DMSO, 80 µL of substrate and 10 µL of enzyme. Each experiment was run three times. Data is an average of these experiments.

Substrate specificity was determined by testing the activity of HL and EL with Thio Phosphatidylethylene glycol (PEG) and Thio-phosphatidylethanolamine (PE).

Assay conditions of assay were as follows. Both substrates for EL were run at 0.03 mol fraction, 10 mM total lipid. They were dissolved in 100 mM Hepes with 9.95 mM TX100. Both substrates for HL were run at 0.06 mol fraction and 7.25 mM total lipid. They were dissolved in 100 mM Hepes with 6.83 mM Triton X100. The EL enzyme was used at 1× and the HL enzyme was used at 0.25×. The order of addition was as follows:10 µL of 10% DMSO, 80 µL of substrate and 10 µL of enzyme. The DMSO and substrate were incubated for 10 minutes at 37° C. before the addition of the enzyme. DTNB was added to the substrate prior to addition to the well at 0.096 mg/mL final plate concentration. The experiments were performed 3 times. Data represents an average of these.

While the present invention has been illustrated above by certain specific embodiments, it is not intended that these specific embodiments should limit the scope of the invention as described in the appended claims.

EXPERIMENTAL

All of the products of the Examples described below as well as intermediates used in the following procedures showed satisfactory NMR and IR spectra. They also had the correct-mass spectral values.

Example 1

3-Oxo-3H-benzo[d]isoxazole-2-carboxylic acid ethylamide

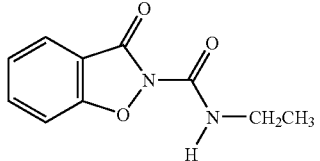

6-1

Ethyl isocyanate (92.4 mg, 1.30 mmol) is added to a stirred solution of benzo[d]isoxazol-3-one (150 mg; 1.10 mmol) in anhydrous THF (4 mL) at ambient temperature under nitrogen. The resultant mixture is heated in an oil bath at 70° C. for 2 hr. After concentration and subsequent flash chromatography on silica (15% hexane in $CH_2Cl_2$), 6-1 is obtained as a white solid (170 mg, 75% yield). mp 112.0–113.0° C.; $^1$H-NMR (CDCl$_3$) δ1.28 (t, J=7.3 Hz, 3H), 3.43–3.51 (m, 2H), 7.21–7.29 (m, 3H), 8.04 (br s, 1H), 8.07 (d, J=6.8 Hz, 1H); ESIMS m/e 207 (M+H)$^+$. Analysis for $C_{10}H_{10}N_2O_3$: calcd: C, 58.25; H, 4.89; N, 13.59; found: C, 58.04; H, 4.82; N, 13.41.

Example 2

3-Oxo-3H-benzo[d]isoxazole-2-carboxylic acid butylamide

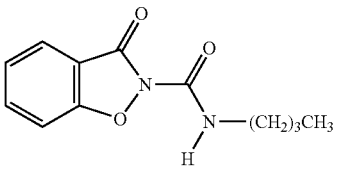

6-2

By following similar procedure as described in Example 1, title compound 6-2 (66% yield) is obtained as a white solid. mp 64.0–65.0° C.; ESIMS m/e 235 (M+H)$^+$. Analysis for $C_{12}H_{14}N_2O_3$: calcd: C, 61.53; H, 6.02; N, 11.96; found: C, 61.30; H, 6.24; N, 11.97.

Example 3

3-Oxo-3H-benzo[d]isoxazole-2-carboxylic acid hexylamide

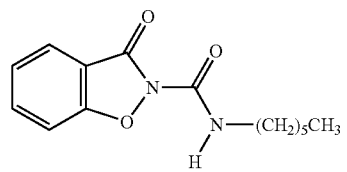

6-3

By following similar procedure as described in Example 1, title compound 6-3 is obtained as a white solid. mp 46.0–48.0° C.; ESIMS m/e 263 (M+H)$^+$.

Example 4

3-Oxo-3H-benzo[d]isoxazole-2-carboxylic acid (5-methyl-hexyl)amide

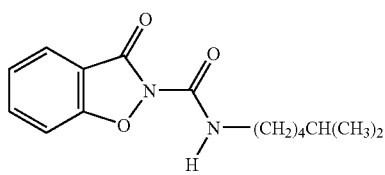

6-4

A. Preparation of (1-isocyanato-5-methyl)-hexane

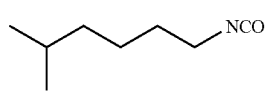

4

A solution of 5-(methyl)hexylamine (407 mg, 3.53 mmol) and proton sponge (1.51 g, 7.06 mmol) in anhydrous CH$_2$Cl$_2$ (6 mL) is added dropwise to a stirred solution of triphosgene (419 mg, 1.41 mmol) in anhydrous CH$_2$Cl$_2$ (6 mL) at 0° C. The resultant solution is allowed to stir at ambient temperature for 15 minutes. After dilution with CH$_2$Cl$_2$ (40 mL), the mixture was washed with 1N HCl (15×2 mL) and water (15 mL). The organic layer is dried over Na$_2$SO$_4$, filtered and concentrated to give the desired isocyanate 4 (365 mg, 73% yield) as oil. $^1$H-NMR (CDCl$_3$) δ0.88 (d, J=6.6 Hz, 6H), 1.16–1.23 (m, 2H), 1.32–1.42 (m, 2H), 1.50–1.62 (m, 3H), 3.29 (t, J=6.6 Hz, 2H).

B. Preparation of 3-oxo-3H-benzo[d]isoxazole-2-carboxylic acid (5-methyl-hexyl)amide

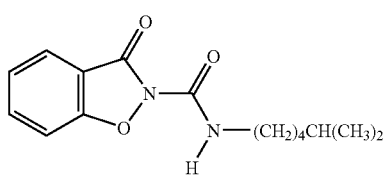

6-4

By following similar procedure as described in Example 1, title compound 6-4 is obtained as a white solid. mp 73.0–75.0° C.; $^1$H-NMR (DMSO-d$_6$) δ0.84 (d, J=6.6 Hz, 6H), 1.14–1.20 (m, 2H), 1.26–1.34 (m, 2H), 1.47–1.55 (m, 3H), 3.26–3.31 (m, 2H), 7.22–7.29 (m, 2H), 7.38–7.41 (m, 1H), 7.86–7.89 (m, 1H), 8.11 (t, J=5.5 Hz, 1H); FDMS m/e 276 (M)$^+$. Analysis for C$_{15}$H$_{20}$N$_2$O$_3$: calcd: C, 65.20; H, 7.30; N. 10.14; found: C, 65.22; H, 7.39; N, 10.18.

Example 5

3-Oxo-3H-benzo[d]isoxazole-2-carboxylic acid octylamide

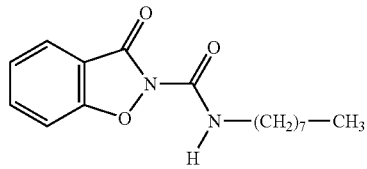

6-5

By following similar procedure as described in Example 1, title compound 6-5 is obtained as a white solid. mp 47.0–48.0° C.; ESIMS m/e 291 (M+H)$^+$.

Example 6

3-Oxo-3H-benzo[d]isoxazole-2-carboxylic acid cyclohexylmethyl-amide

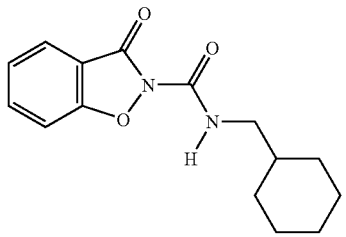

6-6

A. Preparation of 3-oxo-3H-benzo[d]isoxazole-2-carboxylic acid 4-nitro-phenyl ester

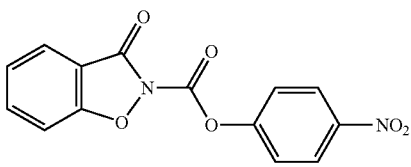

7

A solution of 4-nitrophenyl chloroformate (1.63 g, 7.80 mmol) in anhydrous THF (20 mL) is added to a stirred solution of benzo[d]isoxazol-3-one (1.06 g, 7.80 mmol) in anhydrous THF (20 mL) at 0° C. under nitrogen. Then NEt$_3$ (1.19 mL, 8.50 mmol) is added dropwise to the stirred mixture at 0° C. to form a white suspension. After stirring at 0° C. for 10 minutes, the mixture is filtered and the filtrate is concentrated at ambient temperature in vacuo to give a white solid. The white solid is dissolved in EtOAc (80 mL) and the solution is washed with H$_2$O (25 mL×3), dried over Na$_2$CO$_3$, filtered and concentrated to give a white solid. After recrystallization in THF/hexane, the title compound 7 is obtained as a white solid (1.46 g, 63% yield). Which is used for the subsequent reaction.

B. Preparation of 3-oxo-3H-benzo[d]isoxazole-2-carboxylic acid cyclohexylmethyl-amide

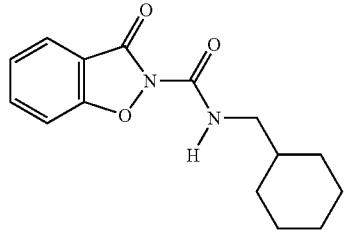

6-6

Cyclohexylmethyl amine (0.070 mL, 0.53 mmol) is added dropwise to a stirred suspension of 3-oxo-3H-benzo[d]isoxazole-2-carboxylic acid 4-nitro-phenyl ester 7 (150 mg, 0.500 mmol) in anhydrous THF (3 mL) at 0° C. under nitrogen to from a clear solution. Then triethyl amine (0.070 mL, 0.50 mmol) is added to the solution and the resultant mixture is allowed to stir at 0° C. for 30 minutes. The mixture is concentrated and the crude product is chromatographed on silica (gradient 10–30% EtOAc in hexane) to give the title compound 6-6 as a white solid. mp 82.0–84.0° C.; ESIMS m/e 275 (M+H)$^+$.

Example 7

3-Oxo-3H-benzo[d]isoxazole-2-carboxylic acid benzylamide

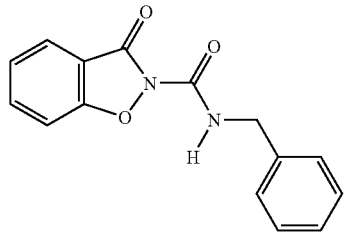

6-7

By following similar procedure as described in Example 1, title compound 6-7 is obtained as a white solid. mp 124;0–125.0° C.; ESIMS m/e 269 (M+H)$^+$.

Example 8

3-Oxo-3H-benzo[d]isoxazole-2-carboxylic acid 2-methyl-benzylamide

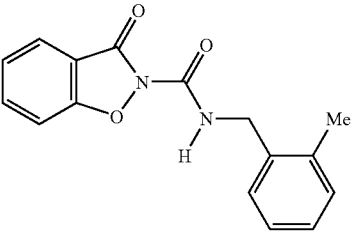

6-8

By following similar procedure as described in Example 6, title compound 6-8 is obtained as a white solid. mp 154.0–155.0° C.; ESIMS m/e 283 (M+H)$^+$.

Example 9

3-Oxo-3H-benzo[d]isoxazole-2-carboxylic acid 3-methyl-benzylamide

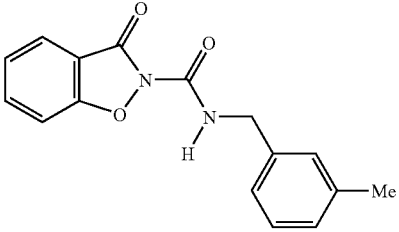

6-9

By following similar procedure as described in Example 6, title compound 6-9 is obtained as a white solid. mp 110.0–112.0° C.; ESIMS m/e 283 (M+H)$^+$. Analysis for $C_{16}H_{14}N_2O_3$: calcd: C, 68.08; H, 5.00; N, 9.92; found: C, 67.89; H, 4.95; N, 10.10.

Example 10

3-Oxo-3H-benzo[d]isoxazole-2-carboxylic acid 4-methyl-benzylamide

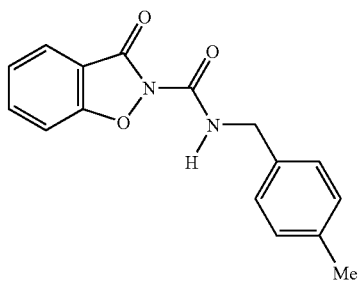

6-10

By following similar procedure as described in Example 6, title compound 6-10 is obtained as a white solid. ESIMS m/e 283 (M+H)$^+$.

Example 11

3-Oxo-3H-benzo[d]isoxazole-2-carboxylic acid 2-trifluoromethyl-benzylamide

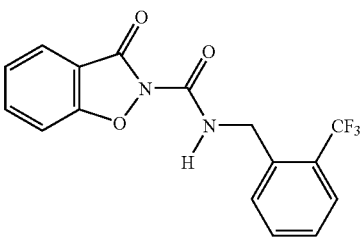

6-11

By following similar procedure as described in Example 6, title compound 6-11 is obtained as a white solid. mp 139.0–141.0° C.; ESIMS m/e 337 (M+H)$^+$. Analysis for $C_{16}H_{11}F_3N_2O_3$: calcd: C, 57.15; H, 3.30; N, 8.33; found: C, 57.13; H, 3.32; N, 8.32

Example 12

3-Oxo-3H-benzo[d]isoxazole-2-carboxylic acid 2-fluoro-benzylamide 6-12

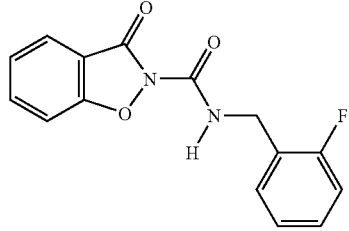

By following similar procedure as described in Example 6, title compound 6-12 is obtained as a white solid. mp 142.0–143.0° C.; ESIMS m/e 287 (M+H)$^+$.

Example 13

3-Oxo-3H-benzo[d]isoxazole-2-carboxylic acid 4-fluoro-benzylamide 6-13

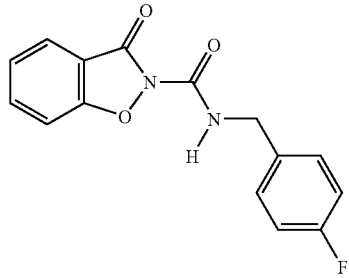

By following similar procedure as described in Example 6, title compound 6-13 is obtained as oil. FDMS m/e 286 (M)$^+$.

Example 14

3-Oxo-3H-benzo[d]isoxazole-2-carboxylic acid 2-ethyl-benzylamide 6-14

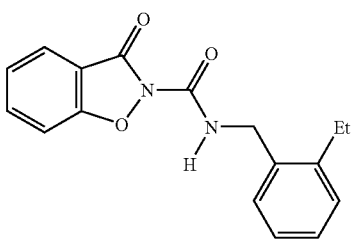

By following similar procedure as described in Example 6, title compound 6-14 is obtained as a white solid. mp 107.0–109.0° C.; ESIMS m/e 314 (M+NH$_4$)$^+$. Analysis for $C_{17}H_{16}N_2O_3$: calcd: C, 68.91; H, 5.44; N, 9.45; found: C, 69.09; H, 5.57; N, 9.39.

Example 15

3-Oxo-3H-benzo[d]isoxazole-2-carboxylic acid 3-ethyl-benzylamide 6-15

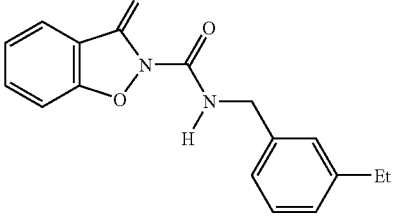

By following similar procedure as described in Example 6, title compound 6-15 is obtained as a white solid. mp 72.0–73.0° C.; FDMS m/e 296 (M)$^+$. Analysis for $C_{17}H_{16}N_2O_3$: calcd: C, 68.91; H, 5.44; N, 9.45; found: C, 69.07; H, 5.53; N, 9.40

Example 16

3-Oxo-3H-benzo[d]isoxazole-2-carboxylic acid 4-tert-butyl-benzylamide 6-16

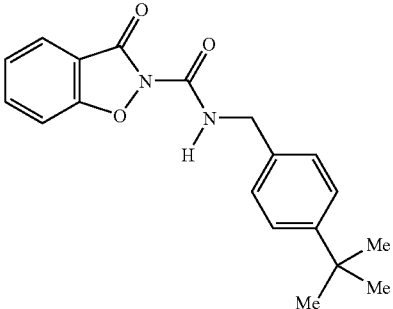

By following similar procedure as described in Example 6, title compound 6-16 is obtained as a white solid. mp 123.0–125.0° C.; FDMS m/e 325 (+H)$^+$.

Example 17

3-Oxo-3H-benzo[d]isoxazole-2-carboxylic acid 2-isopropyl-6-methyl-benzylamide 6-17

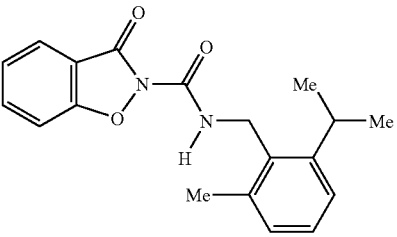

A. The preparation of 2-isopropyl-6-methyl-benzonitrile

2

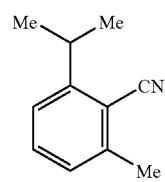

CuCN (7.80 g, 87.2 mmol) is added to a stirred anhydrous DMSO (70 mL) at 60° C. to form a clear solution, then followed by the addition of t-BuNO₂ (24.0 mL, 202 mmol) all at once. A solution of 2-isopropyl-6-menthylaniline (10.0 g, 67.0 mmol) in anhydrous DMSO (30 mL) is added dropwise, via an addition funnel, to the mixture. After the addition is complete, the reaction mixture is allowed to stir for 1 hr. After being cooled to 45° C., the mixture is slowly treated with 5N HCl (100 mL). Five minutes later, the reaction mixture is cooled to ambient temperature before it is extracted with EtOAc/hexane (1:1; 500×2 mL). The combined organic layers are washed with water (100 mL) and brine (100 mL), dried, concentrated in vacuo, then chromatographed on silica (0–5% EtOAc in hexane) to give 8.43 g of the crude nitrile 2. IR(CHCl₃) 2220 cm⁻¹; ¹H-NMR (CDCl₃) δ1.30 (d, J=6.9 Hz, 6H), 2.54 (s, 3H), 3.38 (h, J=6.9 Hz, 1H), 7.13 (br d, J=7.8 Hz, 1H), 7.20 (br d, J=7.8 Hz, 1H), 7.41 (br t, J=7.8 Hz, 1H); ESIMS m/e 160 (M+H)⁺.

B. The preparation of 2-isopropyl-6-methyl-benzylamine

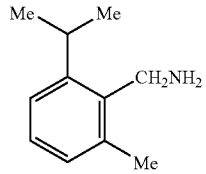

3

To the crude ice-cold nitrile 2 (7.74 g, 48.6 mmol) in anhydrous Et₂O (70 mL) is slowly added lithium aluminum hydride (1N in Et₂O, 97.2 mL) under nitrogen. The resultant mixture is allowed to stir at ambient temperature for 16 hr. Then the reaction mixture is cooled at 0° C. and quenched with MeOH until the gas evolution stops. EtOAc (500 mL) and saturated aqueous Rochelle's salt are added and the two-layered mixture is stirred vigorously under nitrogen for 1 hr to give two relatively clear layers. The organic layer is separated, dried over MgSO₄, filtered and concentrated, the crude oil is chromatographed on silica [20% EtOAc in hexane, then 1–2% (4.2 M Me₃N in EtOH) in CHCl₃]. Amine 3 (3.78 g, yield 48%) is obtained as a brown oil. IR(CHCl₃) 3300(br) cm⁻¹; ¹H-NMR (CDCl₃) δ1.16 (d, J=6.8 Hz, 6H), 1.55 (br s, 2H), 2.33 (s, 3H), 3.28 (h, J=6.8 Hz, 1H), 3.71 (s, 2H), 6.92–6.95 (m, 1H), 7.03–7.10 (m, 2H); ESIMS m/e 164 (M+H)⁺.

C. The preparation of 3-oxo-3H-benzo[d]isoxazole-2-carboxylic acid 2-isopropyl-6-methyl-benzylamide

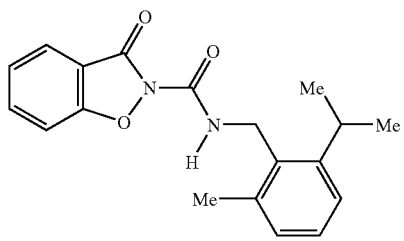

6-17

By following similar procedure as described in Example 6, title compound 6-17 is obtained as a white solid. mp 112.0–114.0° C.; FDMS m/e 324 (M)⁺. Analysis for C₁₉H₂₀N₂O₃: calcd: C, 70.35; H, 6.21; N, 8.64; found: C, 70.37; H, 6.30; N, 8.58.

Example 18

3-Oxo-3H-benzo[d]isoxazole-2-carboxylic acid 3-methoxy-benzylamide

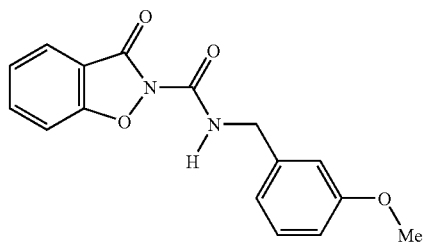

6-18

By following similar procedure as described in Example 6, title compound 6-18 is obtained as a white solid. mp 99.0–100.0° C.; ESIMS m/e 299 (M+H)⁺.

Example 19

3-Oxo-3H-benzo[d]isoxazole-2-carboxylic acid 4-methoxy-benzylamide

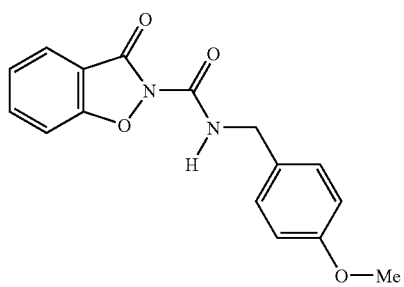

6-19

By following similar procedure as described in Example 6, title compound 6-19 is obtained as a white solid. mp 140.0–141.0° C.; FDMS m/e 298 (M)⁺.

Example 20

3-Oxo-3H-benzo[d]isoxazole-2-carboxylic acid 2-ethoxy-benzylamide

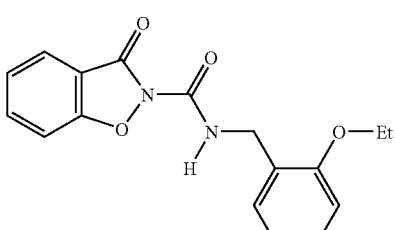

6-20

By following similar procedure as described in Example 6, title compound 6-20 is obtained as a white solid. mp 110.0–112.0° C.; ESIMS m/e 313 (M+H)⁺. Analysis for C₁₇H₁₆N₂O₄: calcd: C, 65.38; H, 5.16; N, 8.97; found: C, 65.33; H, 5.21; N, 8.86.

Example 21

3-Oxo-3H-benzo[d]isoxazole-2-carboxylic acid 3-ethoxy-benzylamide 6-21

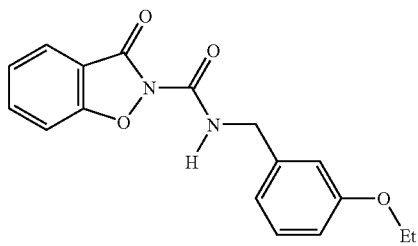

By following similar procedure as described in Example 6, title compound 6-21 is obtained as a white solid. mp 89.0–90.0° C.; ESIMS m/e 313 (M+H)$^+$. Analysis for $C_{17}H_{16}N_2O_4$: calcd: C, 65.38; H, 5.16; N, 8.97; found: C, 65.32; H, 5.18; N, 8.83.

Example 22

3-Oxo-3H-benzo[d]isoxazole-2-carboxylic acid 4-ethoxy-benzylamide 6-22

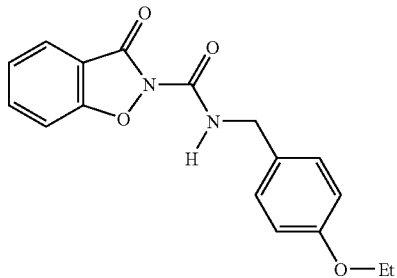

By following similar procedure as described in Example 6, title compound 6-22 is obtained as a white solid. mp 110.0–112.0° C.; FDMS m/e 312 (M)$^+$. Analysis for $C_{17}H_{16}N_2O_4$: calcd: C, 65.38; H, 5.16;. N, 8.97; found: C, 65.17; H, 5.17; N, 8.93.

Example 23

3-Oxo-3H-benzo[d]isoxazole-2-carboxylic acid phenethyl-amide 6-23

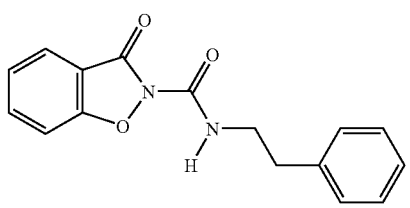

By following similar procedure as described in Example 1, title compound 6-23 is obtained as a white solid. mp 106.0–107.0° C.; FDMS m/e 282 (M)$^+$.

What is claimed is:

1. A 3-oxo-3H-benzo[d]isoxazole carboxamide compound of formula (I):

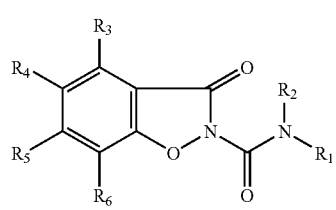

(I)

wherein;

$R_1$ is selected from the group consisting of hydrogen, $C_1$–$C_{13}$alkyl, $C_1$–$C_{20}$haloalkyl, $C_2$–$C_{13}$alkenyl, $C_2$–$C_{20}$alkynyl, $C_1$–$C_{13}$alkoxyalkyl, $C_1$–$C_{13}$alkylamine, $C_1$–$C_5$alkylcycloalkyl, $C_1$–$C_5$alkylcycloalkenyl, cycloalkyl, cycloalkenyl, $C_1$–$C_5$alkylaryl, C(O)$C_1$–$C_6$alkyl, and alkylheterocyclic radical; wherein each of the alkyl, alkenyl, alkynyl, cycloalkyl, cycloalkenyl, and heterocyclic groups may be further substituted with 1, 2, or 3 substituents independently selected from $C_1$–$C_6$alkyl, halo, haloalkyl, COOH, C(O)O$C_1$–$C_6$alkyl, C(O) $C_1$–$C_6$alkyl, hydroxy, and amino groups;

$R_2$ is hydrogen;

$R_3$, $R_4$, $R_5$, and $R_6$, are each independently selected from hydrogen, halo, hydroxy, amino, $C_2$–$C_{12}$alkyl, $C_1$–$C_{12}$haloalkyl, $C_2$–$C_{12}$alkenyl, $C_2$–$C_{12}$alkynyl, $C_2$–$C_{12}$alkylaryl, $C_1$–$C_{12}$alkylcycloalkyl, $C_1$–$C_{12}$alkylcycloalkenyl, COOH, C(O)$C_1$–$C_6$alkyl, C(O) O$C_1$–$C_6$alkyl, C(O)NR$^a$R$^b$$C_1$–$C_{12}$alkylheterocyclic, phenyl, or aryl; wherein R$^a$ and R$^b$ are independently selected from $C_1$–$C_5$alkyl, $C_2$–$C_5$alkenyl, phenyl, benzyl, and $C_1$–$C_5$alkylcycloalkyl; or a pharmaceutically acceptable salt, solvate prodrug or enantiomer thereof.

2. A compound of claim 1 wherein $R_1$ is selected from ($C_3$–$C_{13}$)alkyl, ($C_3$–$C_{14}$)alkenyl, ($C_3$–$C_4$)cycloalkyl, substituted or unsubstituted benzyl.

3. A compound according to claim 1, wherein $R_1$ is 1,5-disubstituted benzyl with substituents independently selected from methyl, ethyl, propyl, isopropyl, isobutyl, and tert-butyl.

4. A compound of claim 1 wherein $R_3$, $R_4$, $R_5$ and $R_6$ are independently selected from hydrogen, ($C_1$–$C_4$)alkyl, ($C_2$–$C_4$)alkenyl, COOH, C(O)O$C_1$–$C_6$alkyl, C(O) $C_1$–$C_6$alkyl —O—($C_1$–$C_3$ alkyl), —S—($C_1$–$C_3$ alkyl), ($C_5$–$C_{20}$)cycloalkyl, —CF$_3$, halo.

5. The compound of claim 1 wherein $R_5$ is the group represented by chloro, bromo, COOH, or CF$_3$.

6. A compound of formula (I) selected from the group consisting of:

3-oxo-3H-benzo[d]isoxazole-2-carboxylic acid ethylamide, 3-oxo-3H-benzo[d]isoxazole-2-carboxylic acid butylamide, 3-oxo-3H-benzo[d]isoxazole-2-carboxylic acid hexylamide, 3-oxo-3H-benzo[d]isoxazole-2-carboxylic acid (5-methyl-hexyl)amide, 3-oxo-3H-benzo[d]isoxazole-2-carboxylic acid octylamide,
3-oxo-3H-benzo[d]isoxazole-2-carboxylic acid cyclohexylmethyl-amide,
3-oxo-3H-benzo[d]isoxazole-2-carboxylic acid benzylamide,
3-oxo-3H-benzo[d]isoxazole-2-carboxylic acid 2-methyl-benzylamide,
3-oxo-3H-benzo[d]isoxazole-2-carboxylic acid 3-methyl-benzylamide,
3-oxo-3H-benzo[d]isoxazole-2-carboxylic acid 4-methyl-benzylamide,
3-oxo-3H-benzo[d]isoxazole-2-carboxylic acid 2-trifluoromethyl-benzylamide,
3-oxo-3H-benzo[d]isoxazole-2-carboxylic acid 2-fluoro-benzylamide,
3-oxo-3H-benzo[d]isoxazole-2-carboxylic acid 4-fluoro-benzylamide,
3-oxo-3H-benzo[d]isoxazole-2-carboxylic acid 2-ethyl-benzylamide,
3-oxo-3H-benzo[d]isoxazole-2-carboxylic acid 3-ethyl-benzylamide,
3-oxo-3H-benzo[d]isoxazole-2-carboxylic acid 4-tert-butyl-benzylamide,
3-oxo-3H-benzo[d]isoxazole-2-carboxylic acid 2-isopropyl-6-methyl-benzylamide,
3-oxo-3H-benzo[d]isoxazole-2-carboxylic acid 3-methoxy-benzylamide,
3-oxo-3H-benzo[d]isoxazole-2-carboxylic acid 4-methoxy-benzylamide,
3-oxo-3H-benzo[d]isoxazole-2-carboxylic acid 2-ethoxy-benzylamide,
3-oxo-3H-benzo[d]isoxazole-2-carboxylic acid 3-ethoxy-benzylamide,
3-oxo-3H-benzo[d]isoxazole-2-carboxylic acid 4-ethoxy-benzylamide,
3-oxo-3H-benzo[d]isoxazole-2-carboxylic acid phen-ethyl-amide, and a pharmaceutically acceptable salt, solvate, racemate, enantiomer or diastereomeric mixture thereof.

7. A 3-oxo-3H-benzo[d]isoxazole carboxamide compound represented by the formulae (C1), (C2), (C3), (C4), and (C5):

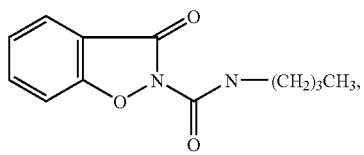
(C1)

-continued

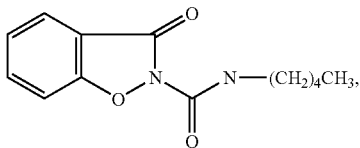
(C2)

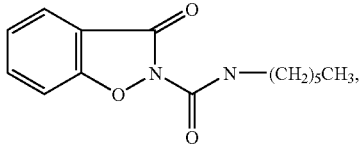
(C3)

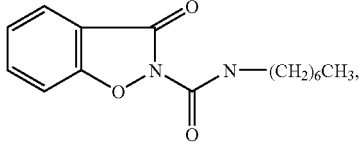
(C4)

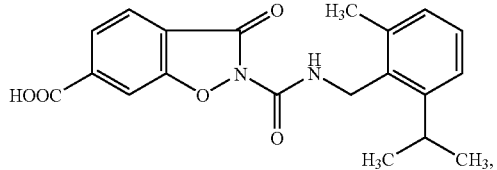
C5 or a pharmaceutically acceptable salt, or solvate, thereof.

8. A pharmaceutical formulation comprising a 3-oxo-3H-benzo [d]isoxazole carboxamide compound of formula I together with a pharmaceutically acceptable carrier or diluent.

9. A method of treating a mammal to alleviate the pathological effects of low HDL associated with elevated hepatic lipase and/or endothelial lipase activity wherein the method comprises administering to said mammal a therapeutically effective amount of a 3-oxo-3H-benzo[d]isoxazole carboxamide compound of formula I.

10. A method of treating a mammal afflicted with low HDL comprising administering to said mammal a therapeutically effective amount of a compound of formula I.

11. A method of preparing a pharmaceutical composition comprising admixing a therapeutically effective amount of a compound according to claim 1 with a pharmaceutically acceptable carrier or diluent.

* * * * *